US007523026B2

(12) United States Patent
Tsuda et al.

(10) Patent No.: US 7,523,026 B2
(45) Date of Patent: Apr. 21, 2009

(54) PROTEOME ANALYSIS METHOD AND PROTEOME ANALYSIS SYSTEM

(75) Inventors: Kenichiro Tsuda, Tokyo (JP); Jiro Shimada, Tokyo (JP); Minoru Asogawa, Tokyo (JP); Kenichi Kamijyo, Tokyo (JP); Toshimasa Yamazaki, Tokyo (JP)

(73) Assignee: NEC Corporation, Tokyo (JP)

( * ) Notice: Subject to any disclaimer, the term of this patent is extended or adjusted under 35 U.S.C. 154(b) by 285 days.

(21) Appl. No.: 10/454,490

(22) Filed: Jun. 5, 2003

(65) Prior Publication Data

US 2003/0228630 A1 Dec. 11, 2003

(30) Foreign Application Priority Data

Jun. 7, 2002 (JP) .............................. 2002-167914

(51) Int. Cl.
G06G 7/48 (2006.01)
(52) U.S. Cl. .............................. 703/11; 703/2; 702/19; 702/23; 702/27; 436/86
(58) Field of Classification Search ........................ None
See application file for complete search history.

(56) References Cited

U.S. PATENT DOCUMENTS

2003/0049715 A1* 3/2003 Welsch et al. .................. 435/23
2003/0068831 A1* 4/2003 Edwards et al. ............. 436/518

FOREIGN PATENT DOCUMENTS

JP 2003-344416 12/2003
WO WO 00/66771 11/2000

OTHER PUBLICATIONS

"Calculate" definition, 2006, Merriam-Webster online dictionary, on the world wide web at http://www.m-w.com/dictionary/calculate, 2 pages.*
"In silico", Wikipedia, on the world wide web at http://en.wikipedia.org/wiki/In_silico, 2006, 2 pages.*
Japanese Office Action dated Dec. 18, 2007 with a partial English translation.

* cited by examiner

Primary Examiner—Carolyn L. Smith
(74) Attorney, Agent, or Firm—McGinn IP Law Group, PLLC

(57) ABSTRACT

A proteome analysis method includes using a tandem type mass spectrometer to calculate bond dissociation energy by using molecular simulation, using the bond dissociation energy to obtain prediction information including a cleavage pattern of a peptide and/or peak positions in a mass spectrum and/or the intensity ratio of the mass spectrum, and identifying a protein by using the prediction information and experiment information.

15 Claims, 14 Drawing Sheets

FIG. 2

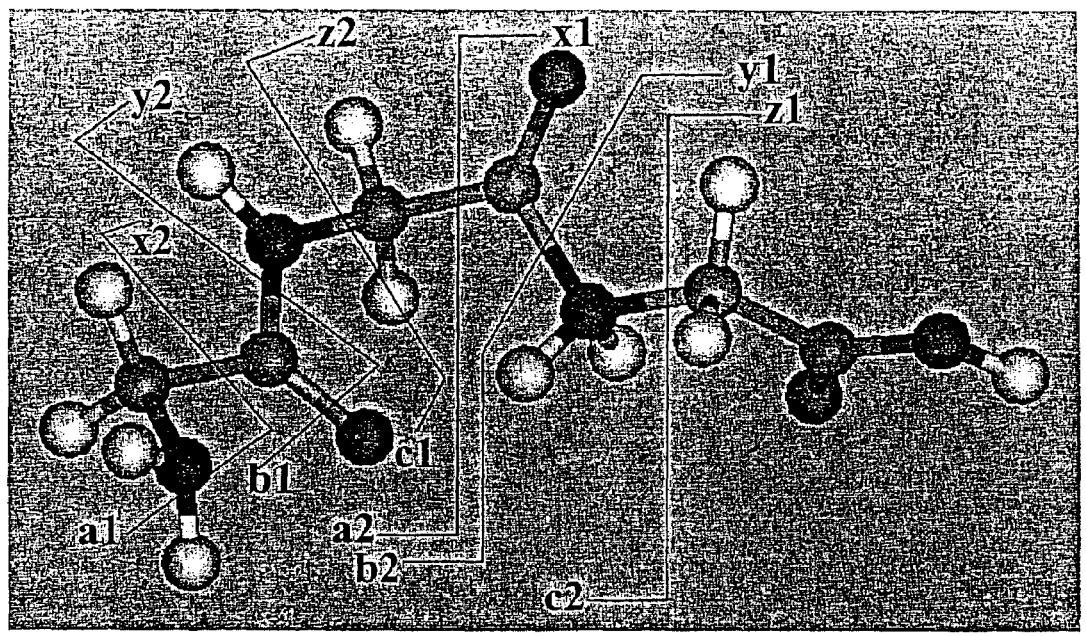

Gly$_3$ + H$^+$ ⟶ Gly$_3$H$^+$ ⟶ ION SERIES

BOND PROTON / CLEAVE (a 1) H$_2$N=CH$_2^+$ + (C=O)NHCH$_2$ C=ONH$_2$CH$_2$COOH
(b 1) H$_2$NCH$_2$(C=O)$^+$ + NH$_2$CH$_2$(C=O)NHCH$_2$COOH
(c 1) H$_2$NCH(C=O)$^+$NH$_2$ + CH$_2$(C=O)NHCH$_2$COOH
(x 1) H$_2$NCH$_2$(C=O)NHCH$_2$ + (C=O)N$^+$H$_2$CH$_2$COOH
(y 1) H$_2$NCH$_2$(C=O)NHCH$_2$(C=O) + H$_3$N$^+$CH$_2$COOH
(z 1) H$_2$NCH$_2$(C=O)NHCH$_2$(C=O)NH$_2$ + CH$_2$=COOH$^+$ (a 2) NH$_2$CH$_2$(C=O)NH$^+$CH$_2$ + OCNH$_2$CH$_2$COOH
(b 2) NH$_2$CH$_2$(C=O)NHCH$_2$(C=O)$^+$ + G l y
(c 2) NH$_2$CH$_2$(C=O)NHCH$_2$(C=O)NH$_2^+$ + CH$_2$COOH
(x 2) NH$_2$CH$_2$ + (C=O)NHCH$_2$(C=O)N$^+$H$_2$CH$_2$COOH
(y 2) NH$_2$CH$_2$(C=O) + H$_2$NCH$_2$(C=O)N$^+$H$_2$CH$_2$COOH
(z 2) NH$_2$CH$_2$(C=O) NH + H$_2$C(O=C)NH$_2$CH$_2$COOH

FIG. 3
A.
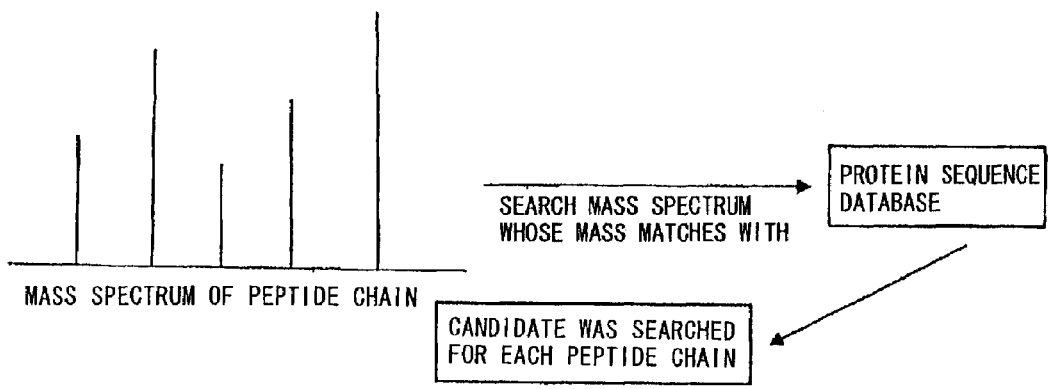
MASS SPECTRUM OF PEPTIDE CHAIN
SEARCH MASS SPECTRUM WHOSE MASS MATCHES WITH → PROTEIN SEQUENCE DATABASE
CANDIDATE WAS SEARCHED FOR EACH PEPTIDE CHAIN
B. MAKE COMBINATIONS OF AMINO ACIDS OF $20^n$
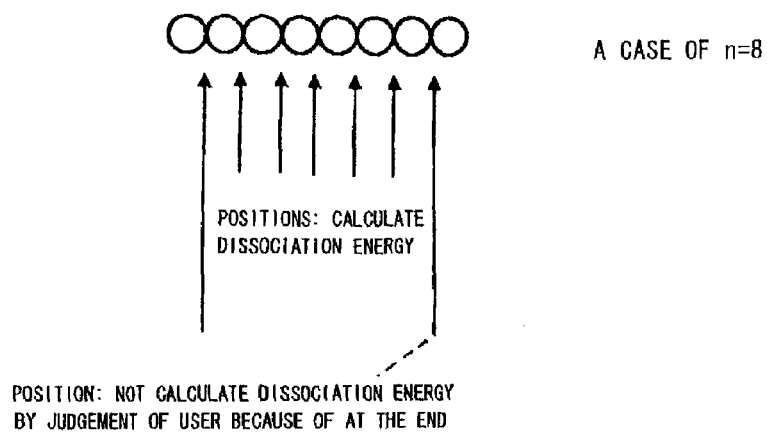
A CASE OF n=8
POSITIONS: CALCULATE DISSOCIATION ENERGY
POSITION: NOT CALCULATE DISSOCIATION ENERGY BY JUDGEMENT OF USER BECAUSE OF AT THE END

F I G. 5

| MOLECULAR ID | BOND DISSOCIATION ENERGY ΔE (Kcal/mol) | ION SERIES | THE NUMBER OF RESIDUES OF WHICK A MOLECULE IS COMPOSED | AMINO ACID SEQUENCE AT N TERMINAL SIDE | AMINO ACID SEQUENCE AT C TERMINAL SIDE | APPROXIMATION METHOD & BASIS FUNCTION | SCORE VALUE (DEGREE OF MATCHING %) |
|---|---|---|---|---|---|---|---|
| 1 | 187.85 | a | 3 | GG | G | HF 631G* | 68 |
| 2 | 44.88 | b | 3 | GG | G | HF 631G* | 15 |
| 3 | 150.42 | c | 3 | GG | G | HF 631G* | 37 |
| 4 | 93.08 | x | 3 | G | GG | HF 631G* | 22 |
| 5 | 53.50 | y | 3 | G | GG | HF 631G* | 9 |
| 6 | 151.60 | z | 3 | G | GG | HF 631G* | 22 |
| .. | .. | .. | .. | .. | .. | .. | .. |

F I G. 6
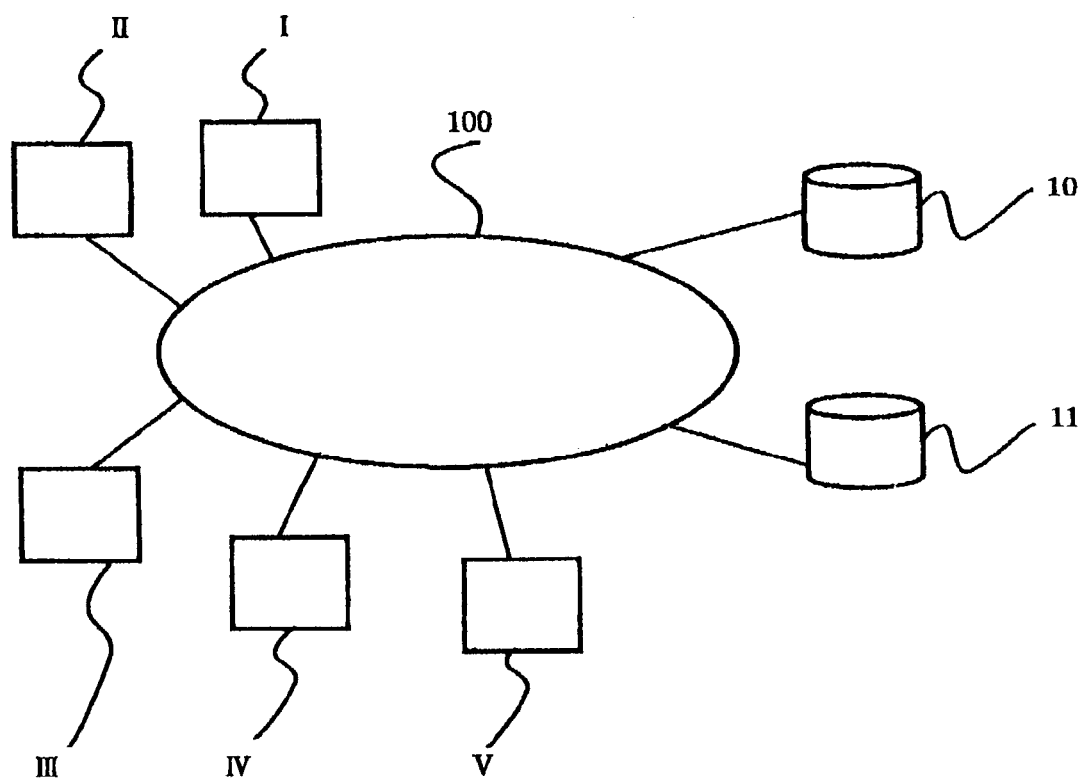

FIG. 8
APPARATUS I
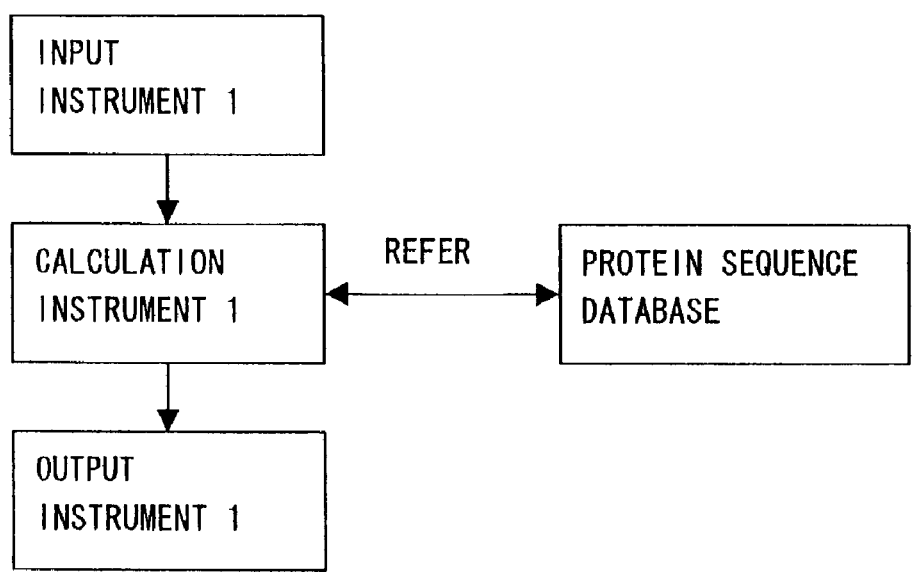
APPARATUS II
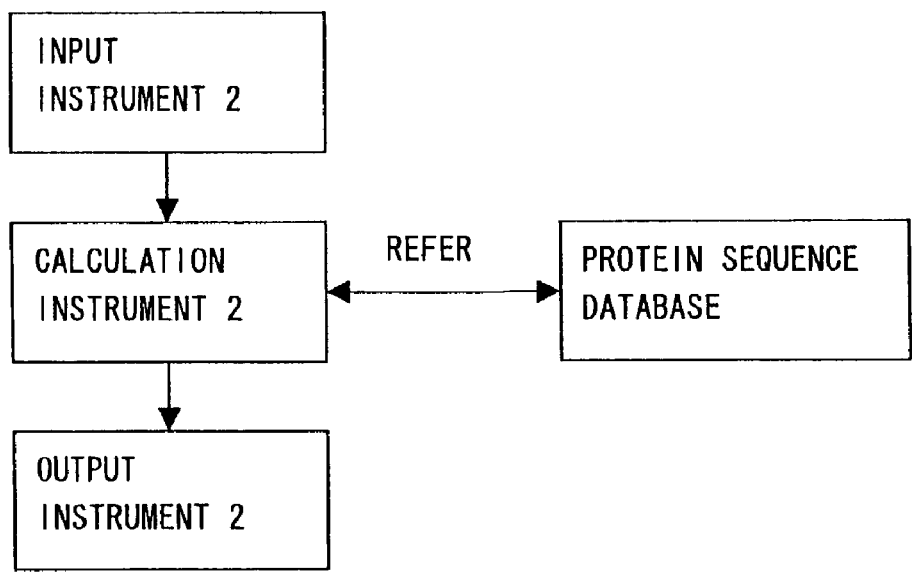

FIG. 9

ProFound – Peptide Mapping [Example]

Version 4.10.5
The Rockefeller University Edition

General

- Sample ID
- Database: NCBInr (2001/12/11)
- Taxonomic Category: ... Saccharomyces cerevisiae
- Search for: single protein only
- Protein Mass: 0 - 3000 kDa
- Protein pI: 0 - 14
- Report Top: 10 Candidates Questions? Please write to ProFound
What's new about ProFound?

Digestion

- Allow maximum 1 missed cleavages
- Enzyme: Trypsin

For user-defined cleavage, please click here.

Modifications

- Complete Modification(s): Unmodified / 4-vinyl-pyridine (Cys) / Acrylamide (Cys) / Iodoacetamide (Cys) / Iodoacetic acid (Cys)
- Partial Modification: ☐ Methionine oxidation For more partial modifications, please click here.

Masses

Average Masses:

| 1041.72 | 1080.03 | 1093.73 |
| 1101.62 | 1111.77 | 1142.07 |
| 1153.01 | 1157.91 | 1192.88 |
| 1230.23 | 1274.33 | 1286.18 |
| 1356.47 | 1371.45 | 1386.38 |

Mass tolerance for average data: +/- 1
Tolerance unit: ● Da ○ % ○ ppm

Monoisotopic Masses:

Mass tolerance for monoisotopic data: +/- 0.1
Charge state: ● M ○ MH+

FIG. 10

Reprints of our posters at the 48th ASMS Conference are available in PDF format (ThPB096, ThPB097).

ProFound – Search Result Summary
Version 4.10.5
The Rockefeller University Edition Protein Candidates for search BE045496-0590-2F78F306 [9644 sequences searched]

| Rank | Probability | Est'd Z | Protein Information and Sequence Analyse Tools (T) | % | pI | kDa |
|---|---|---|---|---|---|---|
| +1 | 1.0e+000 | 2.37 | T gi|6325331|ref|NP_015399.1| (NC_001148) Transketolase 1; Tkl1p [Saccharomyces cerevisiae] | 68 | 6.5 | 73.79 |
| +2 | 1.8e-030 | – | T gi|496731|emb|CAA83584.1| (Z32672) nucleoporin [Saccharomyces cerevisiae] | 16 | 6.5 | 145.39 |
| +3 | 7.5e-031 | – | T gi|227524|prf||1705300A ATP dependent RNA helicase [Saccharomyces cerevisiae] | 37 | 8.4 | 65.63 |
| +4 | 1.3e-031 | – | T gi|728695|emb|CAA88537.1| (Z48618) DNA helicase type protein [Saccharomyces cerevisiae] | 22 | 6.6 | 76.89 |
| +5 | 1.7e-032 | – | T gi|6322807|ref|NP_012980.1| (NC_001143) Dynein; Dyn1p [Saccharomyces cerevisiae] | 9 | 5.9 | 471.33 |
| +6 | 1.1e-032 | – | T gi|2447013|dbj|BAA22509.1| (D37948) defective F1F0-ATPase alpha subunit precursor [Saccharomyces cerevisiae] | 22 | 9.0 | 58.65 |
| +7 | 7.5e-034 | – | T gi|6325172|ref|NP_015240.1| (NC_001148) multidomain vesicle coat protein that interacts with Sec23p; Sec18p [Saccharomyces cerevisiae] | 12 | 5.2 | 241.68 |
| +8 | 2.6e-034 | – | T gi|391941|dbj|BAA02508.1| (D13228) PHO81 [Saccharomyces cerevisiae] | 15 | 5.6 | 134.26 |
| 9 | 5.1e-035 | – | T gi|14318569|ref|NP_116702.1| (NC_001136) Hypothetical ORF; Yfr044cp [Saccharomyces cerevisiae] | 33 | 5.4 | 52.85 |
| +10 | 3.9e-035 | – | T gi|6320433|ref|NP_010513.1| (NC_001136) regulator of silencing at HML, HMR, and telomeres; Sir4p [Saccharomyces cerevisiae] | 18 | 9.1 | 152.04 |

NOTE:
1. To search again using unmatched masses, click the symbol ⓑ.
2. Highly similar protein sequences were given the same rank (IE user: click "+" to expand/contract).

Input Summary

Date & Time Thu Feb 14 11:55:38 2002 UTC (Search Time: 1.14 sec.)
Sample ID
Database NCBInr (2001/12/11)
Taxonomy Category Saccharomyces cerevisiae (baker's yeast)
Protein Mass Range 0 – 3000 kDa
Protein pI Range 0.0 – 14.0
Search for Single protein only
Digest Chemistry Trypsin
Max Missed Cut 1
Modifications None
Charge State M
Peptide Masses 1041.720 1080.030 1093.730 1101.620 1111.770 1142.070 1153.010 1157.910 1192.880
(Da,Average) 1230.230 1274.330 1286.180 1356.470 1371.460 1386.380 1418.450 1430.670 1485.420
1531.460 1608.790 1628.840 1653.890 1670.170 1688.120 1708.080 1740.030 1766.290
1790.980 1869.040 1899.450 1960.290 2028.530 2047.740 2058.130 2105.320 2184.150
2201.950 2261.710 2316.350 2388.560 2429.000 2446.390 2457.630 2473.350 2545.020
2653.750 2604.070 2623.410 2702.620 2718.760 2761.270 2779.970 2805.590 2851.700
2867.830 2944.290 2975.040 3016.440 3028.570 3045.260 3113.170 3221.730 3245.860
3288.720 3345.420 3373.800 3535.190 3852.990 3868.360 3945.840
Tolerance(AVG) 1.00 Da
Peptide Masses
(Da,Monoisotopic)
Tolerance(MON) 0.10 Da
Number of Peptides 70

This ProFound is made available to public through the courtesy of ProteoMetrics. [search + transmission time: >=1.31 sec]

Sample ID : [Pass:0]
Measured peptides : 70
Matched peptides : 29
Min. sequence coverage: 68%

| Measured Mass (M) | Avg/ Mono | Computed Mass | Error (Da) | Residues Start | To | Missed Cut | Peptide sequence |
|---|---|---|---|---|---|---|---|
| 1041.720 | A | 1042.200 | -0.480 | 663 | 671 | 1 | |
| 1041.720 | A | 1042.200 | -0.480 | 315 | 322 | 1 | |
| 1093.730 | A | 1094.279 | -0.549 | 519 | 528 | 0 | |
| 1101.820 | A | 1102.255 | -0.835 | 323 | 332 | 0 | |
| 1142.070 | A | 1142.404 | -0.334 | 238 | 245 | 1 | |
| 1192.880 | A | 1193.284 | -0.404 | 626 | 635 | 0 | |
| 1230.230 | A | 1230.429 | -0.200 | 322 | 332 | 1 | |
| 1356.470 | A | 1356.501 | -0.031 | 648 | 659 | 0 | |
| 1485.420 | A | 1485.663 | -0.243 | 333 | 345 | 1 | |
| 1628.840 | A | 1628.789 | 0.051 | 50 | 62 | 1 | |
| 1688.120 | A | 1687.824 | 0.296 | 529 | 544 | 0 | |
| 1740.030 | A | 1740.896 | -0.866 | 626 | 641 | 1 | |
| 1869.040 | A | 1868.934 | 0.106 | 393 | 410 | 0 | |
| 2028.530 | A | 2028.295 | 0.235 | 642 | 659 | 1 | |
| 2105.320 | A | 2104.390 | 0.930 | 334 | 352 | 1 | |
| 2184.150 | A | 2183.322 | 0.828 | 391 | 410 | 1 | |
| 2201.950 | A | 2201.507 | 0.443 | 585 | 602 | 1 | |
| 2318.350 | A | 2316.571 | 0.779 | 492 | 512 | 0 | |
| 2457.630 | A | 2456.838 | 0.792 | 26 | 49 | 0 | |
| 2473.350 | A | 2472.953 | 0.397 | 603 | 625 | 0 | |
| 2545.020 | A | 2544.805 | 0.215 | 279 | 299 | 1 | |
| 2604.070 | A | 2603.824 | 0.246 | 207 | 229 | 0 | |
| 2851.700 | A | 2851.193 | 0.507 | 246 | 273 | 1 | |
| 2975.040 | A | 2974.280 | 0.760 | 492 | 516 | 1 | |
| 3018.440 | A | 3018.395 | 0.045 | 545 | 574 | 0 | |
| 3113.170 | A | 3112.437 | 0.733 | 177 | 205 | 1 | |
| 3221.730 | A | 3220.737 | 0.993 | 63 | 91 | 0 | |
| 3245.860 | A | 3245.588 | 0.272 | 361 | 390 | 0 | |
| 3373.809 | A | 3373.782 | 0.038 | 360 | 390 | 1 | |
| 3945.840 | A | 3946.394 | -0.554 | 455 | 491 | 0 | |

FIG. 12
APPARATUS III
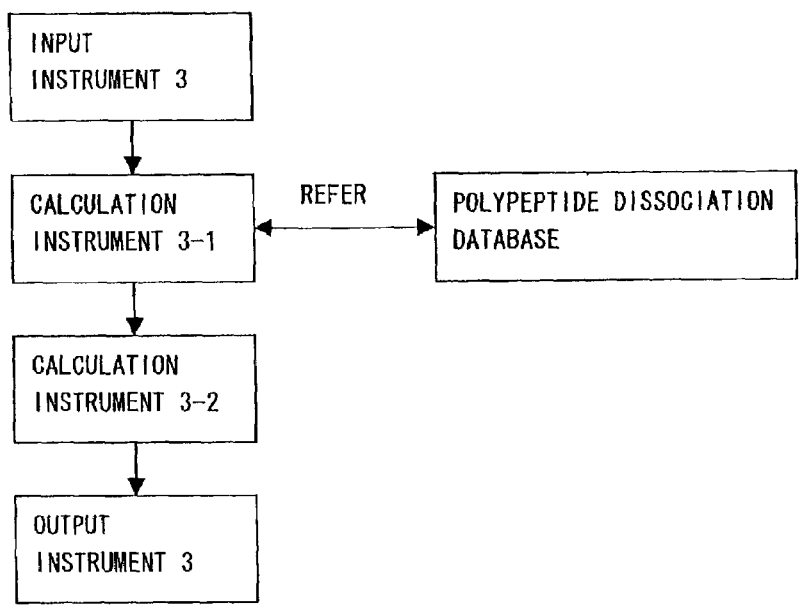
APPARATUS IV
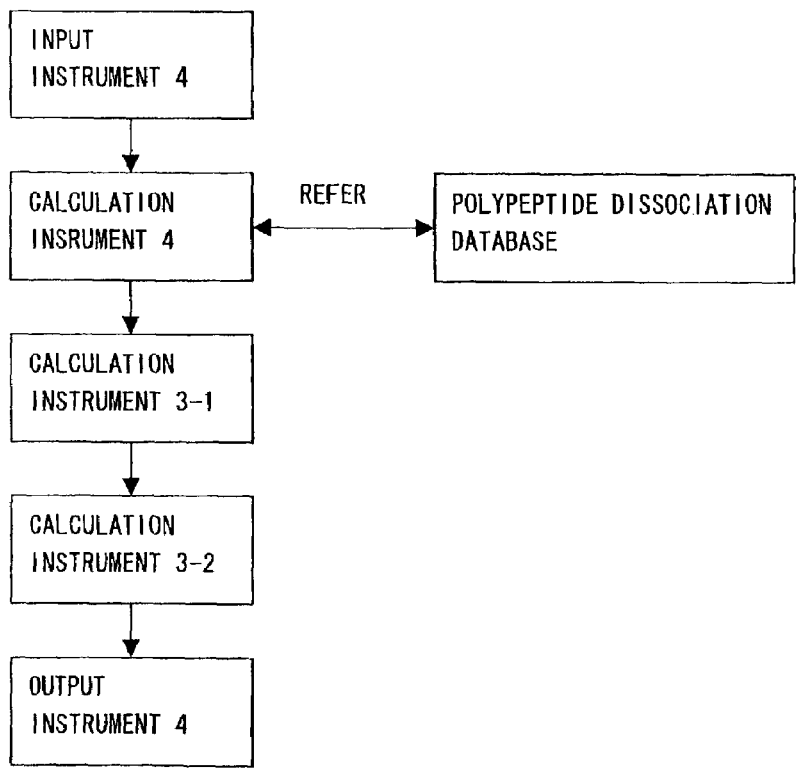

APPARATUS V

PROTEOME ANALYSIS METHOD AND PROTEOME ANALYSIS SYSTEM

BACKGROUND OF THE INVENTION

The present invention relates to a proteome analysis method and a proteome analysis system, which identifies proteins by using a mass spectrometer, in particular, which has the high accuracy and the high throughput, by using predicted results of bond cleavage parts by a molecular simulation method such as a molecular orbital (MO) method.

DESCRIPTION OF THE RELATED ART

In protein identification by using a tandem type mass spectrometer, the protein identification may be executed by the following method. First, a protein is made to be peptides by cleaving with an enzyme, and the mass of each of the peptides is measured by the tandem type mass spectrometer. The obtained each of the peptides of about 5 to 15 residues is made to be fragments, by making a rare gas such as an argon gas collide to each of the peptides or by radiating a laser beam to each of the peptides in the tandem type mass spectrometer, and each of these fragments is dissociated and ionized. And the amino acid sequence of each of the peptides is decided by the mass difference in the peak positions in the obtained mass spectrum. Generally, the pattern of the peak positions is called as a series, b series, c series, and x series, y series, z series, by the cleavage positions. And the protein is identified by matching the experiment data with the existing or known protein sequence database, based on the obtained sequence of each of the peptides.

Generally, 100% closeness (the degree of matching) cannot be obtained, therefore, the degree of matching between the experiment data and the reference data is made to be a score, and a candidate whose score is the largest is adopted. However, there is a case that any of the candidates cannot be adopted, when the scores of all candidates are low.

At a conventional mass spectrometer, the identification of a protein is executed by only using a part of the appeared peak positions, therefore, in some cases, the accuracy of the identification is not enough and has ambiguity. In an extreme case, some identification cannot be executed.

Especially, in case that the identification of a protein is executed by using small samples, the result may not be decided uniquely. In this case, the number of samples must be increased, or it is necessary to experiment several times by trial and error.

In some cases, a mass spectrum, which is considered to appear, does not appear caused by a trouble, or there exist many peaks buried under noise, depending on the experiment conditions. Therefore, there are problems that the high accuracy and the high throughput cannot be obtained at the identification of the protein.

Further, in case that a protein to be identified is a new protein and has not been registered in the protein sequence database, there is a problem that the sequence decision of the protein cannot be executed by a mass spectrometric analysis.

SUMMARY OF THE INVENTION

It is therefore an object of the present invention to provide a proteome analysis method and a proteome analysis system, which identifies proteins by using a mass spectrometer, in particular, which has the high accuracy and the high throughput, by using predicted results of bond cleavage parts by a molecular simulation method such as an MO method.

According to a first aspect of the present invention, for achieving the object mentioned above, there is provided a proteome analysis method by using a tandem type mass spectrometer. At the proteome analysis method, bond dissociation energy is calculated by using a molecular simulation method, and prediction information of a cleavage pattern of a peptide and/or peak positions in a mass spectrum and/or the intensity ratio of the mass spectrum are obtained, and the prediction information is added to experiment information. And the added information is used for identification of a protein.

According to a second aspect of the present invention, in the first aspect, a mass spectrum buried under noise in the mass spectrums obtained by the experiment information and/or, a mass spectrum being difficult to appear under the experiment condition are corrected, and the corrected mass spectrum is used for the identification of the protein.

According to a third aspect of the present invention, in the first aspect, a spectrum pattern is predicted by using the molecular simulation method, for a mass spectrum that cannot be identified by the experiment information because its sequence is known, or for a peptide whose peptide chain, which the protein to be identified was made to be the peptide by an enzyme, has 2 or more residues, or for a protein for which an experiment cannot be executed or in which sufficient accuracy cannot be obtained, and the predicted spectrum pattern is used for the identification of the protein.

According to a fourth aspect of the present invention, in the first aspect, each of the intensity ratios of the mass spectrums is predicted by the estimation value of the bond dissociation energy obtained by using the molecular simulation method.

According to a fifth aspect of the present invention, in the fourth aspect, each of the predicted intensity ratios of the mass spectrums is matched with the experiment information, and the protein is identified.

According to a sixth aspect of the present invention, in the first aspect, the bond dissociation energy in each of ion series calculated by the molecular simulation method is registered in a database, and the database is used for the identification of the protein.

According to a seventh aspect of the present invention, for achieving the object mentioned above, there is provided a proteome analysis system. The proteome analysis system provides a first apparatus, to which an amino acid sequence of a peptide chain or of a protein to be calculated is inputted, refers to a polypeptide dissociation database, and forms a 3-dimensional structure of the amino acid sequence of the peptide chain or of the protein from data of an amino acid sequence of a peptide chain or of a protein that does not exist in the polypeptide dissociation database, and obtains data from the formed 3-dimensional structure, and makes the 3-dimensional structure precise by using the obtained data.

According to an eighth aspect of the present invention, for achieving the object mentioned above, there is provided a proteome analysis system. The proteome analysis system provides a second apparatus, to which the number of amino acids "n" of which a peptide chain or a protein to be calculated is composed, forms at least 1 peptide chain whose peptide chain sequence was predicted, and refers to a polypeptide dissociation database, and forms a 3-dimensional structure of the amino acid sequence of the peptide chain or of the protein from data of an amino acid sequence of a peptide chain or of a protein that does not exist in the polypeptide dissociation database, and obtains data from the formed 3-dimensional structure, and makes the 3-dimensional structure precise by using the obtained data.

According to a ninth aspect of the present invention, in the seventh aspect, the proteome analysis system further provides a third apparatus, to which data of a mass spectrum only obtained from an experiment are inputted, further the position and spectrum intensity of the mass spectrum calculated by the first apparatus are inputted, corrects the mass spectrum obtained from the experiment by scanning the mass spectrum obtained from the experiment on the position and spectrum intensity of the mass spectrum calculated by the first apparatus.

According to a tenth aspect of the present invention, in the eighth aspect, the proteome analysis system further provides a third apparatus, to which data of a mass spectrum only obtained from an experiment are inputted, further the position and spectrum intensity of the mass spectrum calculated by the second apparatus are inputted, corrects the mass spectrum obtained from the experiment by scanning the mass spectrum obtained from the experiment on the position and spectrum intensity of the mass spectrum calculated by the second apparatus.

According to an eleventh aspect of the present invention, in the ninth aspect, the proteome analysis system further provides a fourth apparatus, to which only the mass of a peptide chain or of a protein obtained from the experiment is inputted, matches the mass of the peptide chain or of the protein obtained from the experiment with data in a protein sequence database by referring to the protein sequence database, and outputs a candidate for the amino acid sequence of the peptide chain or of the protein to be identified by using the matched result.

According to a twelfth aspect of the present invention, in the tenth aspect, the proteome analysis system further provides a fourth apparatus, to which only the mass of a peptide chain or of a protein obtained from the experiment is inputted, matches the mass of the peptide chain or of the protein obtained from the experiment with data in a protein sequence database by referring to the protein sequence database, and outputs a candidate for the amino acid sequence of the peptide chain or of the protein to be identified by using the matched result.

According to a thirteenth aspect of the present invention, in the eleventh aspect, the proteome analysis system further provides a fifth apparatus, to which the data of the mass spectrum only obtained from the experiment are inputted, matches the data of the mass spectrum only obtained from the experiment with data in the protein sequence database by referring to the protein sequence database, and outputs a candidate for the amino acid sequence of the peptide chain or of the protein to be identified by using the matched result.

According to a fourteenth aspect of the present invention, in the twelfth aspect, the proteome analysis system further provides a fifth apparatus, to which the data of the mass spectrum only obtained from the experiment are inputted, matches the data of the mass spectrum only obtained from the experiment with data in the protein sequence database by referring to the protein sequence database, and outputs a candidate for the amino acid sequence of the peptide chain or of the protein to be identified by using the matched result.

BRIEF DESCRIPTION OF THE DRAWINGS

The objects and features of the present invention will become more apparent from the consideration of the following detailed description taken in conjunction with the accompanying drawings in which:

FIG. 2 is a diagram showing the relation between cleavage positions and ion series called a, b, c series and x, y, z series at the embodiment of the present invention;

FIG. 3 is a diagram showing methods selecting a peptide chain at the embodiment of the present invention;

FIG. 5 is a diagram showing a data structure of mass spectrum data calculated by a molecular simulation at the embodiment of the present invention;

FIG. 6 is a block diagram showing a structure of a proteome analysis system at the embodiment of the present invention;

FIG. 8 is a block diagram showing structures of apparatuses I and II using at the proteome analysis system at the embodiment of the present invention;

FIG. 9 is a diagram showing an example of inputs for the matching of the mass spectrum data used the identification program ProFound at the embodiment of the present invention;

FIG. 10 is a diagram showing an example of the search result after inputting data shown in FIG. 9;

FIG. 12 is a block diagram showing structures of apparatuses III and IV using at the proteome analysis system at the embodiment of the present invention;

DESCRIPTION OF THE PREFERRED EMBODIMENTS

Figure 1:
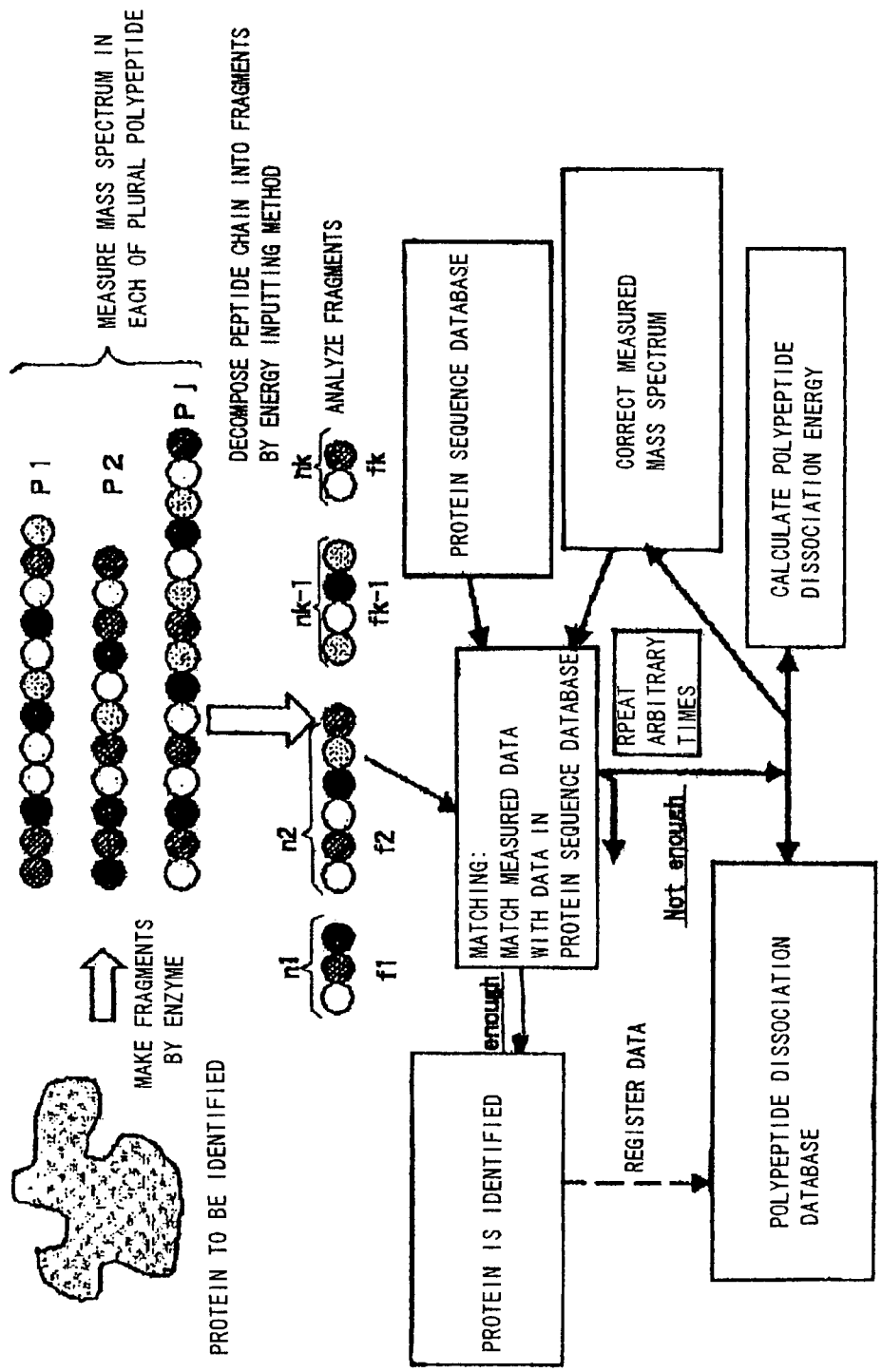
FIG. 1 is a flow diagram showing steps at the identification of a protein at an embodiment of the present invention.

Referring now to the drawings, an embodiment of the present invention is explained in detail. The present invention is a proteome analysis method and a proteome analysis system, in which a new analysis method using a molecular simulation is used at a tandem type mass spectrometer.

FIG. 1 is a flow diagram showing steps at the identification of a protein at the embodiment of the present invention. Referring to FIG. 1, the steps are explained.

First, a protein to be identified is cleaved into plural peptide chains by a biological method using an enzyme, for example, by using the Edman degradation technique. By the enzyme using in this degradation, what peptide bond in a combination of amino acids is cleaved can be predicted.

Next, the mass of each of the cleaved peptide chains is decided by measuring. At this step, the mass is measured but the sequence of each of the peptide chains is not decided. That is; the sequence of the n pieces of amino acid residues is not decided. Next, each of the peptide chains is into fragments $P_1, \ldots, P_j$, by using an arbitrary energy inputting method, for example, a collision induced dissociation (CID) method, or an infrared multiphoton dissociation (IRMPD) method. And the mass of each of the decomposed fragments $P_1, \ldots, P_j$ is analyzed, and experiment data of the mass spectrum of each of the peptide chains are obtained.

FIG. 2 is a diagram showing the relation between cleavage positions and ion series called a, b, c series and x, y, z series at the embodiment of the present invention. As shown in FIG. 2, the spectrum of each of the fragments can be classified into the spectrum series called the a, b, c series or the x, y, z series by the cleaved positions of the peptide chains. For example, when a complete spectrum of the b series appeared, the difference among each of the spectrum positions corresponds to the mass of the composing amino acids, therefore, the amino acid sequence of the peptide chain is decided.

Generally, the difference of the spectrum positions among adjacent the a series, the b series, and the c series becomes a constant value, corresponding to the cleaved positions. Ideally, it is desirable that all of the mass spectrums of the fragments belonging to some series (a, b, c series, x, y, z series) are obtained.

However, actually, there are many cases that the decision of the sequence is difficult. That is, in a case, a part of the fragments that should at least exist was not observed on the spectrum, or in another case, the observed spectrum does not belong to a specific series. In these cases, the mass spectrum obtained by the experiment is corrected by using one of the following molecular simulations.

Next, the method for correcting the mass spectrum obtained by the experiment is explained by using the following seven steps.

At the first step, in order to calculate the bond dissociation energy by using a molecular simulation, a molecule to be calculated is selected. FIG. 3 is a diagram showing methods selecting a peptide chain at the embodiment of the present invention. That is, there are two methods A and B for selecting a peptide chain, and either one of them is selected.

First, the method A for selecting the peptide chain to be calculated is explained. After a protein to be identified was decomposed into a peptide chain, the mass of each of the fragments $P_1, \ldots, P_j$ of the peptide chain was measured by a mass spectrometric analysis. A protein or a peptide chain having an amino acid sequence whose mass matches with the measured mass is searched in a protein sequence database, within the difference designated by the user.

After the result of the search, in case that many candidates exist, the number of the candidates is narrowed, by matching the amino acid sequence predicted by the measured spectrum with the protein sequence database. This process is selected by the user, if necessary. By this method, since the protein sequence database based on the existing information is used, in case that the amino acid sequence has not been registered in the database, or in case that the protein is an unknown protein, it is difficult to identify the protein.

Next, the method B for selecting the peptide chain to be calculated is explained. In order to predict the peak positions and their intensity in the mass spectrum being different among the amino acid sequences by a molecular simulation, combinations of the amino acid sequences whose masses are considered within the same range of the mass of the peptide chain are made. The number of the combinations "n" is not limited, for example, the "n" is 3 or more, or is 5 or more, or "n"=3 to 15, further, "n"=5 to 15, and the combinations can be made by the "n" pieces of the amino acid residues. For example, in case that the "n"=5, the calculation is executed beforehand, and the results of the calculation are registered in a database, this database is explained in detail later. The cleavage positions, which can be calculated, are "n−1" positions, however, the cleavage positions to be calculated can be selected by the user by considering the calculation accuracy. By considering the influence of the surrounding amino acids, it is desirable that a molecular model, in which amino acids of 1 to 2 or 2 or more are attached before and after the cleavage position where the bond dissociation energy is calculated, is considered. At the embodiment of the present invention, the method B is mainly used.

At the second step, the molecular structure of the molecular model selected at the method B of the first step is decided. In this, in case that the CID method was selected as the energy input method for decomposing the peptide chain, after bonding a proton ($H^+$) to a position where electric charge was biased to negative in the molecule, it is known that its dissociation is expedited by the collision of the rare gas. Therefore, a molecular structure where the $H^+$ is bonded is used at the positions where nitrogen atoms and oxygen atoms having high electronegativity exist. Each of the molecules can be some of 3-dimensional structures, therefore, in order to search it, plural structures whose parts are stable can be obtained by using a molecular dynamics (MD) method or a molecular mechanics (MM) method.

In order to obtain a more precise structure, a structure optimizing calculation is executed by the MO method, by using the molecular structure obtained by the MD method or the MM method as its initial value. By the first and second steps mentioned above, data regarding the molecule to be calculated can be obtained. At the calculation by the MO method, an arbitrary approximation method and an arbitrary basis function can be selected. As calculation data for executing the protein identification, it is desirable to use the results calculated by using one of the approximation methods, such as a Hartree-Fock (HF) method, a multi-configuration self consistent field (MCSCF) method, and a configuration interaction (CI) method, and one of the basis functions such as ST0-3G, 3-21G, and 6-31G*. Therefore, at the calculation by the MO method, selected one approximation method and selected one basis function are used. In the database in which the calculated results are registered, the selected approximation method and the selected basis function using at these calculations are described. The database is explained in detail later.

At the third step, the bond dissociation energy of the molecule is calculated. As shown in FIG. 2, the positions of the bond dissociation are decided in each of the series (a, b, c series, and x, y, z series). The a, b, c series the x, y, z series are decided by the following way. Positive charges of peptide ions being the protons bonded to the peptide chains exist at the N terminal side of the fragment ions are called as ions of the b series, on the contrary, exist at the C terminal side are called as ions of the y series. And that —C═O is dropped from the b series ion is called as the a series ion, and that the —C═O is dropped from the y series ion is called as the x series ion.

Generally, the bond dissociation energy is calculated in each of the a, b, c series and the x, y, z series of the molecule. At the actual dissociation experiment, in some cases, internal acyl ions and internal iminium ions shown by $R_2C═N^+R_2$ are generated by internal fragments caused by the plural fragmentation, therefore, when the user judged that it is necessary, this bond dissociation energy is also calculated. In this, the bond dissociation energy for generating these ions is also calculated.

At the fourth step, a peak position pattern of the mass spectrum in each of the combinations of the amino acids is predicted based on the calculated bond dissociation energy. By comparing the selected spectrum positions or the bond dissociation energy of them, a peak position of the fragment generating from the peptide chain having the bond dissociation energy being less than a threshold value designated by the user or a predetermined reference value is adopted.

Figure 4:
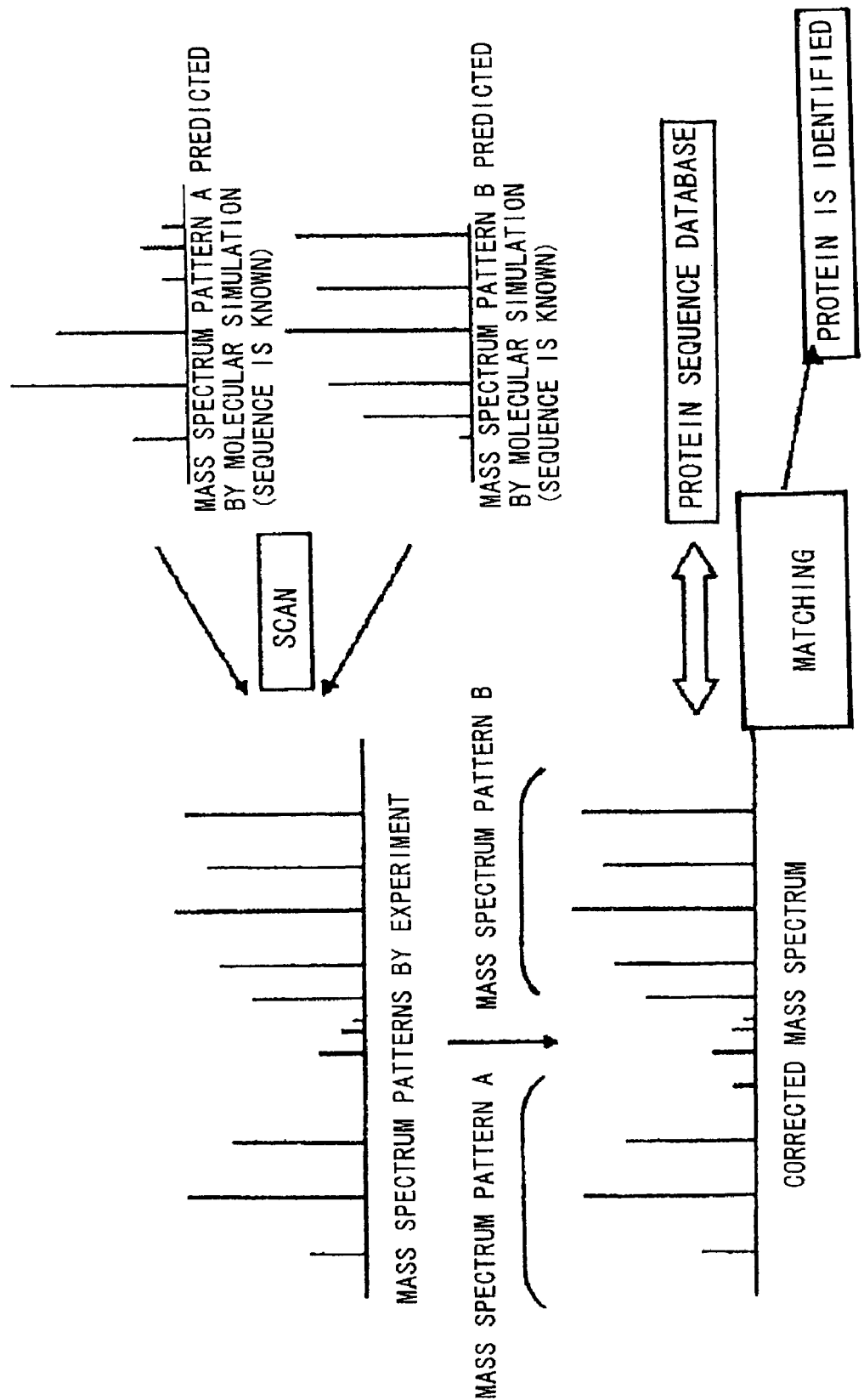
FIG. 4 is a diagram showing a method for correcting the mass spectrum data by a calculation at the embodiment of the present invention.

And based on the bond dissociation energy, the ratio of intensity between the mass spectrums is estimated. Since the ratio of intensity is obtained at this, when the peak position patterns are scanned at the following step, a scaling is applied to the intensity of each of the calculated spectrums, referring to the intensity of the measured spectrums. The patterns of the mass spectrums obtained by the molecular simulation are matched on the patterns of the mass spectrums measured by the experiment. By this matching process, the correction of spectrums being dropped in each of the series is executed, the identification of the spectrums not belonging to the series is executed, the identification of the spectrums buried under noise is executed, and the identification of the spectrums whose origin is unknown is executed. FIG. 4 is a diagram showing a method for correcting the mass spectrum data by a calculation at the embodiment of the present invention. By a reference value designated by the user, as shown in FIG. 4, the complete closeness or the closeness of a part is selected, and the corrected mass spectrum data can be obtained.

At the fifth step, referring to the protein sequence database, the mass spectrum data obtained at the fourth step are matched with the protein sequence database. At this step, an identification program, which is opened in the web site, is used, therefore, this is an existing and known method. The identification programs are opened on the web sites such as MS-FIT and ProFound, by free of charge.

At the sixth step, in case that the identification was not able to be executed at the fifth step, the step returns to the fourth step, and the correction is executed again by changing the level of the correction.

At the seventh step, when the identification of the protein was successful, the bond dissociation energy calculated for each of the molecules, the molecular ID, the ion series, the number of residues of which a molecule being used at the calculation is composed, the amino acid sequence at the N terminal side at the time of dissociation, the amino acid sequence at the C terminal side at the time of dissociation, the name of the approximation method used at the calculation, the name of the basis function, and the score value of the mass spectrum pattern predicted from the calculation are registered in the database. FIG. 5 is a diagram showing a data structure of mass spectrum data calculated by a molecular simulation at the embodiment of the present invention. As shown in FIG. 5, the mass spectrum data are registered in the database.

Referring to FIG. 5, each of the items registered in the database is explained.

The molecular ID: the ID number is attached in order of registration.

The bond dissociation energy: the calculated bond dissociation energy $\Delta E$ is described in kcal/mol.

The ion series: the name of one of the series a, b, c, x, y, and z is given, corresponding to the cleavage position and the existence of ionization.

The number of residues of which a molecule is composed: the number of amino acids of which a molecular model being used at the calculation is composed.

The amino acid sequence at the N terminal side: in order to show the cleavage position, the sequence of the N terminal side viewing from the cleavage position is shown in one letter, for example, even in case that glutamic acid is generally expressed as Glu in its abbreviation, the glutamic acid is expressed as G.

The amino acid sequence at the C terminal side: in order to show the cleavage position, the sequence of the C terminal side viewing from the cleavage position is shown in one letter.

The name of the approximation method: the name is expressed in its abbreviation such as HF, MCSCF, CI, and MP2.

The name of the basis function: the name in which the hyphen is eliminated from the usually using standard basis function at the molecular orbital calculation is described. For example, one of ST03G, 321G, 631G* is shown.

The score value: the degree of matching (the closeness value) between the mass spectrum pattern predicted by the molecular orbital calculation and the known mass spectrum pattern is shown. This closeness value is shown in %. The item of the score value can be selected arbitrarily by the user.

As mentioned at the method B of the first step, in case that the bond dissociation energy was not calculated because the calculation accuracy was considered, the data are not registered in the database. At the embodiment of the present invention, the number of residues "n" of the peptide to be calculated is decided corresponding to the accuracy of the using mass spectrometer, and the data of the "n" pieces of peptide chains are calculated beforehand, and the calculated data are registered in the database.

FIG. 6 is a block diagram showing a structure of a proteome analysis system at the embodiment of the present invention. By using the system, a proteome analysis method at the embodiment of the present invention is executed. As shown in FIG. 6, the proteome analysis system at the embodiment of the present invention consists of apparatuses I to V. In FIG. 6, a protein sequence database 10, a polypeptide dissociation database 11, and a network 100 are also shown. And as shown in FIG. 6, the apparatuses I to V, the protein sequence database 10, and the polypeptide dissociation database 11 are connected via the network 100.

Figure 7:
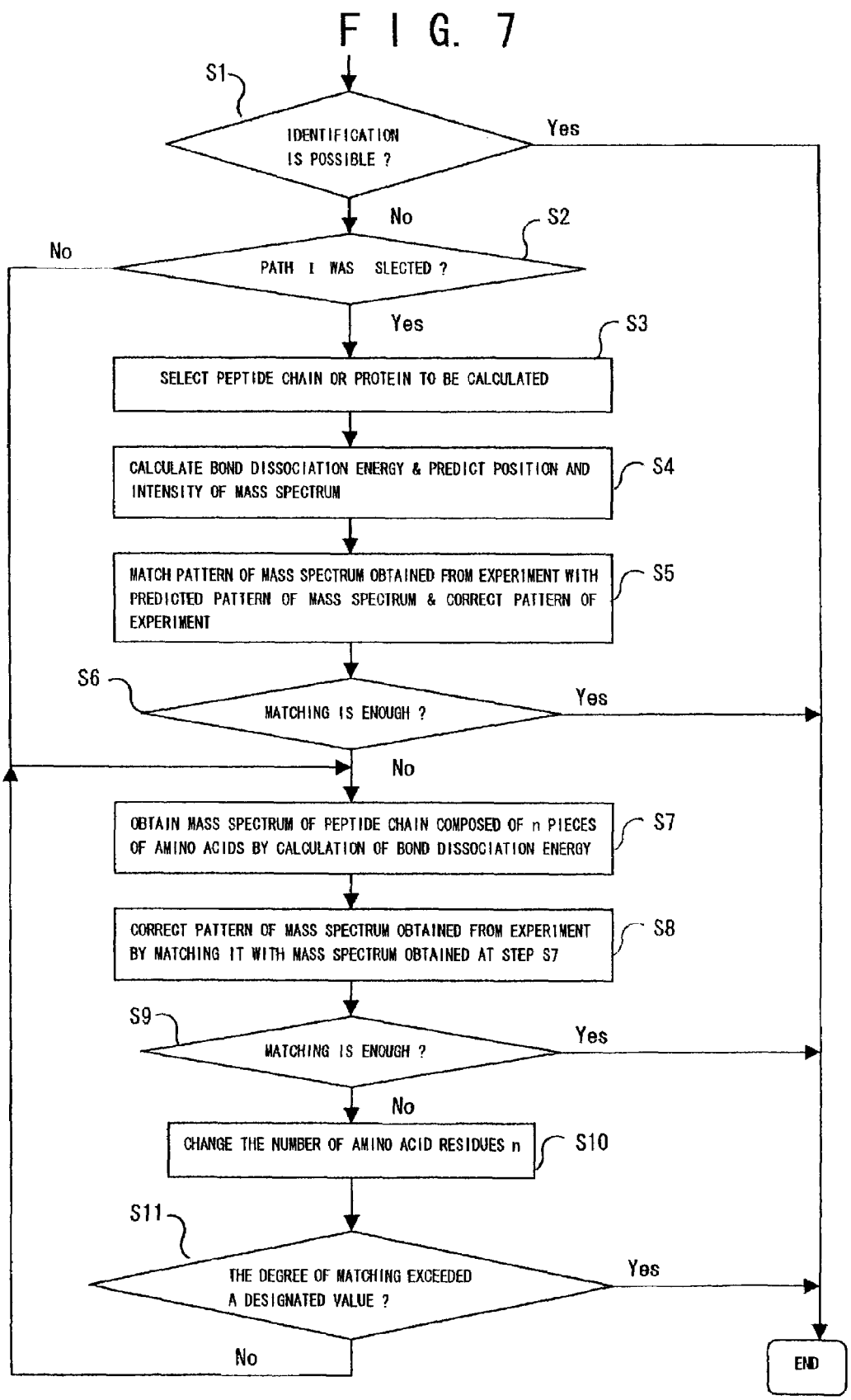
FIG. 7 is a flowchart showing the operation at the proteome analysis method at the embodiment of the present invention.

FIG. 7 is a flowchart showing the operation at the proteome analysis method at the embodiment of the present invention. By using the proteome analysis system shown in FIG. 6, the analysis of a proteome is executed. That is, at least one of the amino acid residues of a protein being one of the components of a proteome is analyzed.

Referring to FIG. 7, the operation of the proteome analysis method at the embodiment of the present invention is explained. Each of the apparatuses I to V is explained in detail later.

At the proteome analysis method, in the apparatus I, first, it is judged whether the identification of a protein by using only experiment data is possible or not (step S1), when it was judged that the identification was possible (Yes at the step S1), the identification of the protein is executed by using only the experiment results (data obtained by the experiment). At the step S1, for identifying the protein, the protein sequence database is used, and the experiment data is matched with the protein sequence database.

When it was judged that the identification was not possible (No at the step S1), this case includes a case in which the identification was not enough because the accuracy of the identification was lower than that of the user requirement, a path I or a path II is selected (step S2). In this case, the user selects the path I or the path II.

Next, a case that the path I was selected is explained. In case that there is a high possibility that the protein has been registered in the protein sequence database, the path I was selected (Yes at the step 2). When the path I was selected, a peptide chain or a protein to be calculated is selected by the apparatus II (step S3). Next, the bond dissociation energy of each of chemical bonds of the peptide chain is calculated by the apparatus III, and the position and the intensity of the mass spectrum are predicted (step S4). And at the apparatus V, the pattern of the mass spectrum obtained by the experiment is matched with the pattern of the mass spectrum predicted from the calculation at the step S4, and if necessary, the experiment results (data obtained by the experiment) are corrected by using the predicted data obtained by the calculation (step S5).

And it is judged whether the matching executed at the step S5 is enough or not (step S6). That is, it is judged whether the identification of the protein is enough or not at the step S6.

When the identification executed above was not enough because the accuracy was low (No at the step S6), that is, the matching was not enough, at the apparatus IV, the mass spectrum of the peptide chain composed of n pieces of amino acids is obtained by the calculation of the bond dissociation energy of the molecule (protein molecule or peptide) (step S7). And at the apparatus V, the pattern of the mass spectrum obtained by the experiment is corrected by using the pattern of the mass spectrum obtained at the step S7, and these patterns are matched with each other (step S8).

And it is judged whether the matching executed at the step S8 is enough or not (step S9). That is, it is judged whether the identification of the protein is enough or not at the step S9.

In case that the matching executed above was not enough from the reason such as the low accuracy (No at the step S9), the number of amino acid residues "n" is changed (step S10). And the operation returns to the step S7 by the apparatus IV, and the operation of "m" times is repeated. At this time, the number of residues "n" of the amino acids and the number "m" of repeating times can be designated by the user. When the degree of matching shown in FIG. 5 became a value exceeded a designated value, it can be judged that the identification was executed. In this case, even the number "m" of repeating times was designated by the user, when it was judged that the degree of matching became the designated value (Yes at step S11), the identification of the protein is completed.

Further, the judgement at the step S11 can be executed at the time when the number "m" of repeating times exceeded a specific value, and the operation at the step S11 can be omitted in some cases. In case that the step S11 was omitted, the judgement of the identification is executed at the step S9.

At the embodiment of the present invention, in case that the degree of matching does not exceed the designated value even when the number "m" of repeating times was changed several times, the operation for the identification (analyzing the proteome, the identification of the amino acid sequence or the identification of the protein) can be finished. Further, the changing times of the number "m" of the repeating times can be set arbitrarily.

Next, a case that the path II was selected is explained. In case that the possibility, which the protein has been registered in the protein sequence database, is low or nothing, the path II was selected. At the path II, the mass spectrum of the peptide chain composed of n pieces of amino acids is estimated by the calculation of the bond dissociation energy of the molecule (protein molecule or peptide) by the apparatus IV. And the pattern of the mass spectrum obtained by the experiment is corrected by the apparatus V as the same as at the path I and the pattern of the mass spectrum obtained by the experiment is matched with the pattern of the estimated mass spectrum by the apparatus V. At this time, as the same as at the path I, the number of residues "n" of the amino acids and the number "m" of repeating times can be designated by the user. And the operation is the same at the steps S7 to S11 at the path I.

Next, referring to the drawings, the apparatuses I to V using at the proteome analysis system at the embodiment of the present invention are explained in detail.

First, the apparatus I (the fifth apparatus) is explained in detail. FIG. 8 is a block diagram showing structures of the apparatuses I and II using at the proteome analysis system at the embodiment of the present invention. As shown at the upper side of FIG. 8, the apparatus I provides an input instrument 1, a calculation instrument 1, and an output instrument 1. Mass spectrum data of fragments being the experiment results are inputted to the input instrument 1. The calculation instrument 1 extracts the inputted mass spectrum data of fragments whose protein is identified and mass spectrum data being the candidates by referring to the protein sequence database, and executes matching for the two mass spectrum data. As the calculation instrument 1, an existing one can be used, for example, one opened on the Internet can be used. The output instrument 1 outputs the name of the candidate protein or the peptide chain, and its amino acid sequence. The apparatus I can be a personal computer (PC), which is started and operated by application software for working as the apparatus I.

Figure 11:
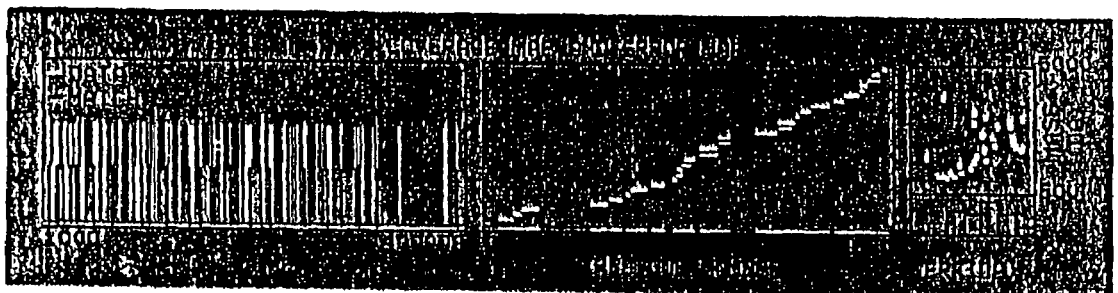
FIG. 11 is a diagram showing an example of the matching result after inputting data shown in FIG. 9.

FIG. 9 is a diagram showing an example of inputs for the matching of the mass spectrum data used the identification program ProFound at the embodiment of the present invention. As shown in FIG. 9, the mass spectrum data (average masses) being the experiment results obtained by a mass spectrometer, the name of an enzyme using for making a peptide chain from a protein, the taxonomic category of the origin of the protein, and matching control parameters are inputted. FIG. 10 is a diagram showing an example of the search result after inputting data shown in FIG. 9. FIG. 11 is a diagram showing an example of the matching result after inputting data shown in FIG. 9. As shown in FIGS. 10 and 11, the search result and the matching result were obtained by inputting basic items. As mentioned above, this identification is executed by using the existing identification program ProFound.

The calculation instrument 1 executes matching between the mass spectrum data being the obtained experiment results and the protein sequence database.

Next, the apparatus II (the fourth apparatus) is explained in detail. As shown at the lower side of FIG. 8, the apparatus II provides an input instrument 2, a calculation instrument 2, and an output instrument 2. The structure of the apparatus II is almost equal to that of the apparatus I, however, the mass value of each of polypeptides (P1, . . . Pn) obtained at the first stage in the tandem type mass spectrometer is inputted to the input instrument 2. And the calculation instrument 2 makes the mass value data inputted from the input instrument 2 match with the mass values in the protein sequence database within the difference range designated by the user. And the matched amino acid sequence of the peptide chain or the protein, and the positions of the modified parts and the modified substituents are outputted from the output instrument 2.

The input instrument 2, the calculation instrument 2, and the output instrument 2 provided in the apparatus II are explained in detail. The input instrument 2 is an instrument for inputting the mass of a peptide chain formed by decomposing the protein to be identified by an enzyme, measured by the first stage mass spectrometer in the tandem type mass spectrometer.

The calculation instrument 2 is an instrument that makes the mass value data inputted from the input instrument 2 match with the mass values in the protein sequence database within the difference range designated by the user, and selects the matched peptide chain or protein.

The output instrument 2 is an instrument that outputs the amino acid sequence of the peptide chain or the protein selected at the calculation instrument 2 and also outputs the positions of the modified parts and the modified substituents.

Next, the apparatus III (the first apparatus) is explained in detail. FIG. 12 is a block diagram showing structures of the apparatuses III and IV using at the proteome analysis system at the embodiment of the present invention. As shown at the upper side of FIG. 12, the apparatus III provides an input instrument 3, a calculation instrument 3-1, a calculation instrument 3-2, and an output instrument 3.

The calculation instrument 3-1, to which the amino acid sequence of a peptide chain or a protein to be calculated was inputted, selects a peptide chain or a protein not existing in the polypeptide dissociation database, referring to the polypeptide dissociation database. Next, a 3-dimensional structure forming calculation is executed based on the molecular dynamics. Further, in order to make the calculated plural 3-dimensional structures more precise, a 3-dimensional structure optimizing calculation is executed by using an ab initio molecular orbital method. And at the calculation instrument 3-2, the bond dissociation energy of all the parts to be calculated is calculated by using the ab initio molecular orbital method, and a reaction rate constant is calculated by using the obtained bond dissociation energy. With this, the intensity of each of the dissociation patterns is calculated.

The input instrument 3, the calculation instrument 3-1, the calculation instrument 3-2, and the output instrument 3 provided in the apparatus III are explained in detail.

The input instrument 3 is an instrument to which the amino acid sequence of which a polypeptide chain is composed is inputted.

The calculation instrument 3-1 is an instrument that forms a 3-dimensional structure of the peptide chain or the protein based on the inputted amino acid sequence.

The calculation instrument 3-2 is an instrument that calculates the bond dissociation energy and the intensity of the mass spectrum.

The output instrument 3 is an instrument that outputs the mass spectrum having the position and intensity estimated by the calculation. This instrument can output the calculated data to the polypeptide dissociation database.

Next, the apparatus IV (the second apparatus) is explained in detail. As shown at the lower side of FIG. 12, the apparatus IV provides an input instrument 4, a calculation instrument 4, a calculation instrument 3-1, a calculation instrument 3-2, and an output instrument 4. The calculation instrument 3-1 and the calculation instrument 3-2 are the same ones at the apparatus III.

The apparatus IV is used at the time when a peptide chain to be calculated cannot be decided. For example, at the first mass spectrometric analysis, the mass data of a peptide chain or a protein was obtained, but the data has not been registered in the protein sequence database, consequently, the amino acid sequence of the protein was not able to be decided. In this case, the apparatus IV is used.

By using the input instrument 4, the user inputs the number of amino acid residues "n", of which the peptide chain to be calculated is composed. Next, at the calculation instrument 4, groups of peptide chains, which are composed of "n" pieces of amino acid residues, are formed, and already calculated groups are eliminated referring to the polypeptide dissociation database. And at the calculation instrument 3-1, for the polypeptides which are not calculated, a 3-dimensional structure forming calculation is executed based on the molecular dynamics. Further, in order to make the calculated plural 3-dimensional structures more precise, a 3-dimensional structure optimizing calculation is executed for each of the plural 3-dimensional structures by using an ab initio molecular orbital method.

And at the calculation instrument 3-2, the bond dissociation energy of all the parts that have dissociation possibility is calculated by using the ab initio molecular orbital method. Further, by using the calculated bond dissociation energy, the mass spectrum corresponding to each of the dissociation patterns is calculated. And the mass spectrum having the calculated position and intensity and also data to be registered in the polypeptide dissociation database are outputted from the output instrument 4.

The input instrument 4, the calculation instrument 4, and the output instrument 4 provided in the apparatus IV are explained.

The input instrument 4 is an instrument from which the user inputs the number of amino acids of which a polypeptide chain to be calculated is composed.

The calculation instrument 4 is an instrument that calculates, referring to the polypeptide dissociation database.

The output instrument 4 is an instrument that outputs the mass spectrum having the positions and intensity estimated by the calculation, and also outputs the data to be registered to the polypeptide dissociation database.

Figure 13:
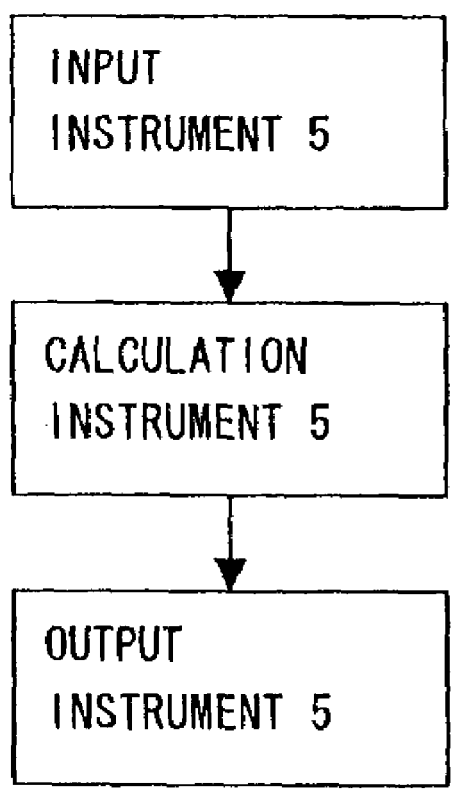
FIG. 13 is a block diagram showing a structure of an apparatus V using at the proteome analysis system at the embodiment of the present invention.

Next, the apparatus V (the third apparatus) is explained in detail. FIG. 13 is a block diagram showing a structure of the apparatus V using at the proteome analysis system at the embodiment of the present invention. As shown in FIG. 13, the apparatus V provides an input instrument 5, a calculation instrument 5, and an output instrument 5.

First, at the input instrument 5, the mass spectrum obtained by the experiment and the position and intensity of the mass spectrum estimated by the calculation are inputted. And at the calculation instrument 5, the mass spectrum obtained from the calculation is scanned on the mass spectrum obtained from the experiment, and the spectrum patterns of both the mass spectrums are matched with each other. And the mass spectrum obtained from the experiment is corrected by the result of the matching. And based on the reference designated by the user, the corrected mass spectrum having the position and intensity is outputted.

The input instrument 5, the calculation instrument 5, and the output instrument 5 provided in the apparatus V are explained.

The input instrument 5 is an instrument from which the mass spectrum obtained by the experiment and the positions and intensity of the mass spectrum estimated by the calculation are inputted.

The calculation instrument 5 is an instrument that scans the mass spectrum estimated from the calculation on the mass spectrum obtained from the experiment, and applies matching for both the spectrum patterns of the mass spectrums. And the mass spectrum obtained from the experiment is corrected. At the matching, for example, by not changing the position of a spectrum estimated to have been dropped in the mass spectrum obtained from the experiment, and the intensity at the position in the spectrum is corrected. And the spectrum data being estimated to have been dropped (spectrum position and spectrum intensity) are added to the mass spectrum data obtained from the experiment.

The output instrument 5 is an instrument that outputs the corrected spectrum data including the intensity and the data to be registered to the polypeptide dissociation database.

The proteome analysis method of the present invention can be executed by using the proteome analysis system mentioned above. At the structures of the apparatuses I to V of which the proteome analysis system is composed, plural input instruments in the input instruments 1 to 5 can be made to be common, and also the input method is not limited. And also at the output instruments and the calculation instruments in the apparatuses I to V, as the same as the input instruments, some of these instruments can be made to be common arbitrarily.

Moreover, a user terminal or a client is used as each of the input instruments, and a server is used as each of the calculation instruments and output instruments, and the protein sequence database and the polypeptide dissociation database are connected to the server via the Internet. This structure of the proteome analysis system is possible.

Furthermore, the input instruments and the calculation instruments and the output instruments are positioned at a client, and the protein sequence database and the polypeptide dissociation database are positioned at a server, and the client and the server are connected via the Internet. This structure of the proteome analysis system is possible.

And the input instruments and the calculation instruments and the output instruments and the polypeptide dissociation database are positioned at a client, and the protein sequence database is positioned at a server, and the client and the server are connected via the Internet. This system structure is also possible.

The apparatuses I to V can be one unit or plural units, and these apparatuses can be connected via a local area network (LAN) or a wide area network (WAN), that is, the apparatuses I to V can be unified, or each of the apparatuses I to V can be independent, or some of the apparatuses I to V can be combined.

As mentioned above, the structure of the proteome analysis system shown in FIG. 6 is an example, the structure can be formed arbitrarily.

Figure 14:
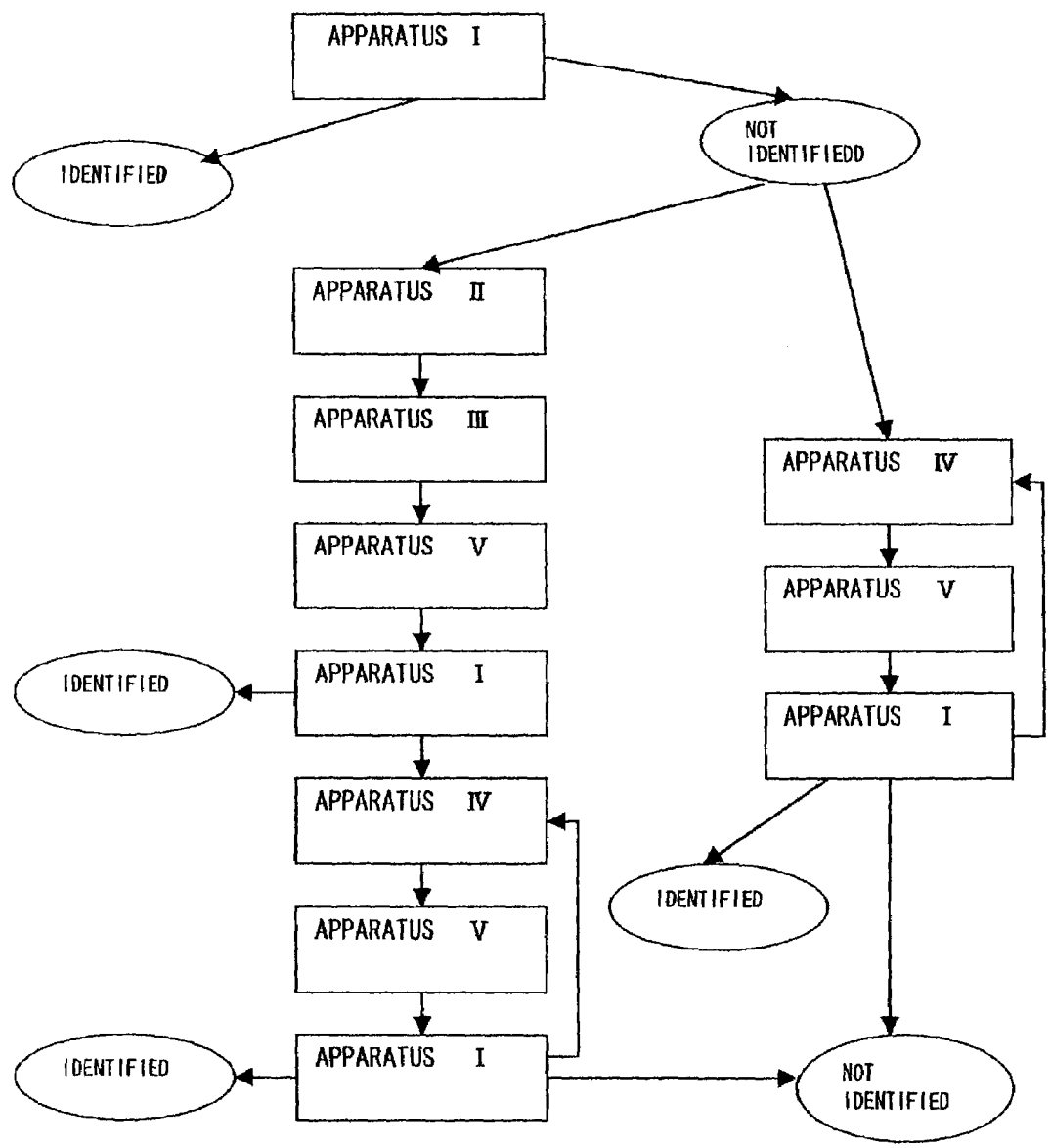
FIG. 14 is a block diagram showing an example of the system structure of the proteome analysis system at the embodiment of the present invention.

FIG. 14 is a block diagram showing an example of the system structure of the proteome analysis system at the embodiment of the present invention. In this case, plural apparatuses are connected. However, the structure of the proteome analysis system can be formed arbitrarily.

At the proteome analysis system of the present invention, it is desirable that all of the apparatuses I to V are provided in the system. However, as the structure of the proteome analysis system, only one of the apparatuses I to V is provided in the system, or arbitrary two or more of the apparatuses I to V are provided in the system, these system structures are also possible.

For example, the proteome analysis system can be composed of the apparatuses II, III, and V. Or the proteome analysis system can be composed of the apparatuses IV, V, and I. Further, the proteome analysis system can be composed of the apparatuses II, III, V, and I.

And the functions of the apparatuses I to V can be realized by software, instead of by hardware, except the input and output functions. That is, application software for the functions of the apparatuses I to V is started and operated from hardware or a ROM (recording media such as CD-ROM, DVD-ROM, and a recording medium down loaded via the Internet) in a PC, with this the functions can be used.

As mentioned above, according to the proteome analysis system and the proteome analysis method at the embodiment of the present invention, the ambiguity at the identification of a protein at the conventional protein identification is eliminated as much as possible by using the mass spectrometric analysis method. In order to achieve the high accuracy and the high throughput at the identification of the protein at the present invention, a cleavage pattern in a peptide is predicted by using a molecular simulation method, such as the MO method, the MD method, and the MM method. And the predicted mass spectrum pattern is used for matching. That is, the present invention is supported by the molecular simulation. And the high accuracy can be obtained by that the appeared peak position m/z (m: mass, z: the number of electric charges) and also the relative intensity of the peak are used at the matching of the mass spectrums. This relative intensity is estimated by the MO method, the MD method, or the MM method. The relative intensity can be also obtained by using the reaction rate or the reaction rate constant, for example, the rate is a rate in which each of fragments is decomposed by the CID method or the IRMPD method. In this, the matching the mass spectrum data obtained by the experiment with the protein sequence database is executed by an existing method. As mentioned above, several protein identification programs are opened at web sites on the Internet. By using one of these programs, the peak position data of the mass spectrum obtained by the experiment are inputted, and the candidate of the protein for the identification is outputted with a score value of the degree of matching (closeness). With this, the identification of the protein can be executed with the high accuracy and the high throughput at the present invention.

As mentioned above, according to the embodiment of the present invention, the identification of a protein can be executed in the high accuracy and the high speed, compared with the conventional method, in which the identification of the protein is executed by using only the peak positions of a part of the mass spectrum. And at the conventional method, only the protein sequence database is referred, and in case that a protein is not an existing and known protein that has been registered in the protein sequence database, the identification of the protein was impossible. However, at the embodiment of the present invention, even when the spectrum of the peptide chain has not been registered in the protein sequence database, the spectrum pattern of the protein can be predicted. Therefore, even a case that the identification of a protein was impossible at the conventional method, the possibility to identify the protein becomes large at the present invention.

Moreover, at an experiment, even a case that a spectrum, which cannot be observed under the conditions of the experiment, exists, or a spectrum, which is judged as noise, exists, this spectrum is calculated at the embodiment of the present invention. And the calculated spectrum position and intensity (intensity ratio) are matched with the spectrum position and intensity obtained from the experiment, and the experiment spectrum is corrected. And by using this corrected data, the identification of the amino acid sequence of the protein or the polypeptide (fragments of peptide) can be executed. At this calculation, for example, a method to obtain intensity (ratio) by using a reaction rate (reaction rate constant) can be adopted.

While the present invention has been described with reference to the particular illustrative embodiment, it is not to be restricted by that embodiment but only by the appended claims. It is to be appreciated that those skilled in the art can change or modify the embodiment without departing from the scope and spirit of the present invention.

What is claimed is:

1. A proteome analysis method, comprising:

calculating bond dissociation energy for a molecule by performing molecular simulation;

obtaining prediction information comprising a cleavage pattern of a peptide of a mass spectrum of protein or peptide chain, based on said calculated bond dissociation energy;

estimating intensity ratio of said mass spectrum, based on said calculated bond dissociation energy;

determining an identity of a protein or peptide chain based on said cleavage pattern, said intensity ratio and experimental mass spectrum data obtained by a mass spectrometer; and outputting to a user said identity of said protein or peptide chain.

2. The proteome analysis method in accordance with claim 1, wherein said determining said identity of said protein or peptide chain comprises matching said cleavage pattern and said intensity ratio with said mass spectrum obtained from an experiment.

3. The proteome analysis method in accordance wit claim 1, wherein said intensity ratio is estimated by at least one of a molecular orbital method, a molecular dynamics method and a molecular mechanics method.

4. The proteome analysis method in accordance with claim 1, wherein said intensity ratio is obtained based on a rate of reaction in which each fragment is decomposed.

5. The proteome analysis method in accordance with claim 1, further comprising:
registering in a database said bond dissociation energy in each ion series calculated by said molecular simulation method,
wherein said determining said identity of said protein or peptide chain comprises referring to said database to determine said identity of said protein or peptide chain.

6. A proteome analysis system, comprising:
a first unit that calculates bond dissociation energy for a molecule by performing molecular simulation;
a second unit that obtains prediction information comprising a cleavage pattern of a peptide of a mass spectrum of protein or peptide chain, based on said calculated bond dissociation energy;
a third unit that estimates intensity ratio of said mass spectrum, based on said calculated bond dissociation energy;
a fourth unit that determines an identity of a protein or peptide chain based on said cleavage pattern, said intensity ratio and experimental mass spectrum data obtained by a mass spectrometer; and
an output device for outputting to a user said identity of said protein or peptide chain.

7. The proteome analysis system in accordance with claim 6, wherein said fourth unit determines said identity of said protein or peptide chain by matching said cleavage pattern and said intensity ratio with said mass spectrum obtained from an experiment.

8. The proteome analysis system in accordance with claim 6, wherein said intensity ratio is estimated by at least one of a molecular orbital method, a molecular dynamics method and a molecular mechanics method.

9. The proteome analysis system in accordance with claim 6, wherein said intensity ratio is obtained based on a rate of reaction in which each fragment is decomposed.

10. The proteome analysis system in accordance with claim 6, further comprising:
a registering unit that registers in a database said bond dissociation energy in each ion series calculated by said molecular simulation method,
wherein said fourth unit refers to said database to determine said identity of said protein or peptide chain.

11. A programmable storage medium tangibly embodying a program of machine-readable instructions executable by a computer to perform a proteome analysis method, said method comprising:
calculating bond dissociation energy for a molecule by performing molecular simulation;
obtaining prediction information comprising a cleavage pattern of a peptide of a mass spectrum of protein or peptide chain, based on said calculated bond dissociation energy;
estimating intensity ratio of said mass spectrum, based on said calculated bond dissociation energy;
determining an identity of a protein or peptide chain based on said cleavage pattern, said intensity ratio and experimental mass spectrum data obtained by a mass spectrometer; and
outputting to a user said identity of said protein or peptide chain.

12. The storage medium for storing a computer program in accordance with claim 11, wherein said determining said identity of said protein or peptide chain comprises matching said cleavage pattern and said intensity ratio with said mass spectrum obtained from an experiment.

13. The storage medium for storing a computer program in accordance with claim 11, wherein said intensity ratio is estimated by at least one of a molecular orbital method, a molecular dynamics method and a molecular mechanics method.

14. The storage medium for storing a computer program in accordance with claim 11, wherein said intensity ratio is obtained based on a rate of reaction in which each fragment is decomposed.

15. The storage medium for storing a computer in accordance with claim 11, further comprising:
a process for registering in a database said bond dissociation energy in each ion series calculated by said molecular simulation method,
wherein said determine said identity of said protein or peptide chain comprises referring to said database to determine said identity of said protein or peptide chain.

* * * * *